United States Patent
Smiley

(12) 
(10) Patent No.: US 6,323,153 B1
(45) Date of Patent: Nov. 27, 2001

(54) METHOD FOR THE CONTROL OF VEGETATION USING HERBICIDAL COMPOSITION CONTAINING CARBOXYLIC OR PHOSHONIC ACID SALT

(75) Inventor: Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 0 days.

(21) Appl. No.: 09/349,073

(22) Filed: Jul. 8, 1999

Related U.S. Application Data

(63) Continuation-in-part of application No. 09/250,775, filed on Feb. 12, 1999, now abandoned.
(60) Provisional application No. 60/092,901, filed on Jul. 15, 1998.

(51) Int. Cl.$^7$ ............................. A01N 37/00; A01N 57/00
(52) U.S. Cl. ............................................ 504/194; 504/320
(58) Field of Search ...................... 504/320, 194

(56) References Cited

U.S. PATENT DOCUMENTS

| | | | |
|---|---|---|---|
| 3,998,967 | 12/1976 | Weil | 424/316 |
| 4,786,307 | * 11/1988 | Marihart | 71/11 |
| 5,668,086 | * 9/1997 | Tadayuki et al. | 504/235 |

FOREIGN PATENT DOCUMENTS

| 0 760 207 A1 | 3/1997 | (EP) . |
|---|---|---|

OTHER PUBLICATIONS

Chemical Abstracts; Junko, et al,; "Herbicides Copntaining Fatty Acids and Ethylenediaminetetraacetic Acid Salts and Weed Control With the Herbicides"; Nov. 20, 1995; Nov. 123, No 21.

Derwent Publications Ltd.; Japan Tobacco, Inc.; "Herbidide Which is Safe to Human Body—Contg. Tropolone Salt and/or Hinokitiol Slat and EDTA Salt"; London, GB; AN 1995-212841.

Chemical Abstracts; Turner, D.J., et al.; "Complexing Agents as Herbicide Additives"; Nov. 6, 1978; vol. 89, No. 19; Columbus, Ohio USA.

Chemical Abstracts; Anon; "Effect of Di– and Trivalent Cations on the Herbicidal Activity of N–Phosphonomethylglycine"; Dec. 20 1976; vol. 85, No. 25; Columbus, Ohio USA.

* cited by examiner

*Primary Examiner*—S. Mark Clardy
(74) *Attorney, Agent, or Firm*—Locke Lidell & Sapp LLP

(57) ABSTRACT

A method for selectively controlling undesirable vegetation by contacting the leaves with a herbicidal composition comprising a carboxylic or phosphonic acid salt known to form a coordination compound with calcium or magnesium salts. In a preferred embodiment, the carboxylic or phosphonic acid salt is an alkali salt of at least one acid selected from an aminopolycarboxylic acid, an aliphatic carboxylic acid, a hydroxycarboxylic acid, an amino acid, an ether polycarboxylic acid, a phosphonic acid and a polyphosphonic acid.

20 Claims, No Drawings

METHOD FOR THE CONTROL OF VEGETATION USING HERBICIDAL COMPOSITION CONTAINING CARBOXYLIC OR PHOSHONIC ACID SALT

This is a continuation-in-part application of U.S. patent application Ser. No. 09/250,775, filed Feb. 12, 1999 now abandoned, which is based on Provisional Application No. 60/092,901, filed Jul. 15, 1998.

FIELD OF THE INVENTION

The present invention relates to the use of a selective herbicidal composition containing a carboxylic or phosphonic acid salt.

BACKGROUND OF THE INVENTION

Chemicals used to kill plants can be classified as either non-selective herbicides or selective herbicides. Non-selective herbicides kill all plants to which they are applied. An example of a non-selective herbicide is N-(phosphonomethyl) glycine, known commonly as gly-phosphate or "Roundup®." A selective herbicide kills only certain plants, that is, it is more toxic to some plants than to others. To be of practical use, a selective herbicide must have the ability to kill undesirable plants without affecting the remaining desirable plants. An example of such a chemical is the well known herbicide 2,4-dichlorophenoxyacetic acid (2,4-D) which will selectively kill broad-leaved weeds in, for example, turf grass. However, there are many weeds which are not destroyed by 2,4-D. Furthermore, 2,4-D is toxic and can cause eye irritation and gastrointestinal disturbances if ingested. Some undesirable grasses, like crabgrass or bermudagrass, can be selectively removed from turf by the use of arsenic compounds, but these herbicides can be toxic to both humans and animals. Other turf weeds, such as nimblewill, are not affected by 2,4-D or arsenic compounds and can only be controlled chemically by using glyphosphate which kills not only the nimblewill but all of the desirable plants surrounding the nimblewill.

U.S. Pat. No. 5,668,086, herein incorporated by reference, discloses the use of a herbicidal composition containing diquat (1,1'-ethylene-2,2'-bipyridinium dibromide) or paraquat (1,1'-dimethyl-4,4'-bipyridinium dichloride) as contact herbicides. Diquat and paraquat have no selectivity but exhibit strong week-killing power by foliage treatment. In use, they are diluted with water. An ionic surfactant is further added so that the liquid can be applied evenly and ensure contact with the stems and leaves of the vegetation long enough to penetrate into the plant body. Unfortunately, the addition of the surfactant lowers the herbicidal effects of the composition. The reduction observed in the herbicidal effects observed in the composition is dependent upon the kind and amount of anionic surfactant used.

It is the primary object of this invention to provide a method for the selective control of certain undesirable vegetation using herbicides which are non-toxic to humans, animals and insects. It is a further object to provide such herbicides that also are odorless, water soluble and biodegradable.

SUMMARY OF THE INVENTION

Undesired vegetation may be killed by wetting the leaves of the vegetation with a herbicidally effective amount of a composition comprising water and a carboxylic or phosphonic acid salt known to form coordination compounds with calcium or magnesium ions. Coordination compounds are substances with chemical structures in which a central metal atom such as calcium is surrounded by groups of non-metallic atoms joined to it by chemical bonds.

Examples of the salts of acids which form complexes with calcium or magnesium ions and are useful in the invention are salts of at least one carboxylic or phosphonic acid selected from aminopolycarboxylic acids, aliphatic carboxylic acids, hydroxycarboxylic acids, amino acids, ether polycarboxylic acids, phosphonic acids and polyphosphonic acids.

The compositions of the invention act as selective herbicides. The composition may further contain a surfactant as well as other conventional adjuvants. Since the mode of action appears to be through the leaves of the vegetation, there is little, if any, residual herbicidal effect in the ground. Thus, it is possible to grow desirable plants adjacent to and around the treated area.

DETAILED DESCRIPTION OF PREFERRED EMBODIMENTS

Unwanted vegetation may be killed by wetting the locus of the vegetation with an aqueous composition containing a carboxylic or phosphonic acid salt known to form coordination compounds with calcium or magnesium ions. In a preferred embodiment, the invention relates to a herbicidal composition containing, as the carboxylic acid salt, the salt of carboxylic or phosphonic acids selected from aminopolycarboxylic acids, aliphatic carboxylic acids, hydroxycarboxylic acids, amino acids, ether polycarboxylic acids, phosphonic acids and polyphosphonic acids.

The carboxylic and phosphonic acids for use in the composition include aminopolycarboxylic acids having from 1 to about 10 carbon groups, a $C_1$–$C_8$ aliphatic carboxylic acid, a $C_1$–$C_8$ hydroxycarboxylic acid, an amino acid and ether polycarboxylic acids having from two to about 10 carbon atoms. The phosphonic acids for use in the invention include phosphonic and polyphosphonic acids having between from two to about 12 carbon atoms.

Suitable for use as the salt are alkali metals, especially sodium, potassium, and lithium, as well as ammonium and amine. In addition, mixtures of these cations can be employed. The amines used to form the salts can be represented by the formula $N(R)_3$ or $N(R)_4^+$ wherein R is independently selected from hydrogen or a $C_1$–$C_8$ alkyl group, a $C_6$–$C_{14}$ aryl group or a $C_7$–$C_{16}$ alkaryl or alkaryl group.

It is not necessary that the carboxylic or phosphonic acid salt be completely neutralized to be effective for use in the invention since only one of the acid groups of a polycarboxylic acid need be in the salt form.

Representative examples of the aminopolycarboxylic acid salts include salts of ethylenediaminetetraacetic acid (EDTA), nitrilotriacetic acid (NTA), iminodiacetic acid (IDA), N-(2-hydroxyethyl)iminodiacetic acid (HIMDA), diethylenetriaminepentaacetic acid ((DTPA), N-(2-hydroxyethyl) ethylenediaminetriacetic acid (EDTA-OH) and glycol ether diaminetetraacetic acid (GEDTA).

Examples of the aliphatic acid salts include salts of oxalic acid, succinic acid, glutaric acid, and pyruvic acid. Exemplary of the amino acid salts include salts of glycine, alanine and lysine. Examples of the hydroxycarboxylic acid salts are salts of malic acid, citric acid, glycolic acid, lactic acid and tartaric acid.

Examples of the phosphonic acid salts include salts of iminodimethylphosphonic acid (IDP), alkyldiphosphonic acids (ADPAs) and polyphosphonic acid.

The herbicidal composition for use in the invention may further contain a mixture of two or more of the carboxylic or phosphonic acid salts referenced herein.

The active herbicidal composition is prepared by dissolving the carboxylic or phosphonic acid salt in water. The herbicide salt solution can also be prepared by mixing the free acid in water and adding the required basic compound (for example, lithium hydroxide, sodium hydroxide, sodium carbonate, sodium bicarbonate, potassium hydroxide, ammonium hydroxide, amine or quaternary ammonium hydroxide) in a sufficient amount to neutralize one or more of the acid groups. The addition could also be reversed, that is, the acid may be added to a water mixture of the required amount of basic compound.

The undesirable vegetation is then treated by wetting the leaves with the resulting herbicidal composition. Death of the wetted undesirable plants occur within one day to one week depending upon ambient temperature and the growing season of the undesirable plants. The younger the plant, the more susceptible it is to be killed. Under certain conditions, more than one treatment may be required to obtain complete control.

Weeds and grasses which may be controlled by the method of this invention include oxalis, quakegrass, crabgrass, bermudagrass, nimblewill, and speedwell.

The amount of carboxylic or phosphonic acid salt in the herbicidal composition varies with the weed to be destroyed and generally ranges from about 0.5 to about 20 wt. percent. The most effective concentration of carboxylic or phosphonic acid salt in the herbicidal composition is between from 1 and about 10 wt. percent. The effectiveness of weed control with the herbicides of the invention also depends on the ambient temperature at the time of treatment. The warmer the weather, the more effective is the desired control.

The amount of herbicidal composition applied to the targeted vegetation is generally between from about 25 to about 150 lbs. per acre.

A surfactant may be added to the solution to aid in wetting the leaves of the treated plants but is not necessary to achieve effective control of the undesired vegetation. Surfactants increase the wetting ability of the composition for plant foliage and facilitate the distribution of the composition to the foliage. Either ionic or non-ionic surfactants may be used. Illustrative of classes of stable surfactants are nonionics such as the ethylene oxides condensates such as of alkylphenols or fatty alcohols and lignosulfonates, ammonium salts of mixtures of aromatic sulphone sulphonic acids condensed with formaldehyde; anionic surfactants such as 1-hydroxyethyl-2-heptadecenyl gloxalidin as well as amine oxide surfactant. The concentration of surfactant should be at least about 0.05, generally at least about 0.1, and preferably at least about 0.2 weight percent of the herbicidal composition.

The composition for use in the invention may further contain other additives such as coloring agents, thickeners and the like. Herbicidal compositions for use in the invention are non-toxic and biodegradable. For example, the salts of EDTA are widely used in household and industrial cleaners, as antioxidants in food and in the treatment of heavy metal poisoning in both humans and animals. Disodium citrate is used in medicine as an anticoagulant to prevent the clotting of blood intended for transfusion.

The carboxylic or phosphonic acid salt for use in the invention is readily available commercially at low cost. Since the only solvent needed is water, the cost of the final herbicidal solution is very low.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

A 1% solution of tetrasodium ethylenediaminetetraacetate was prepared by dissolving 10 g. of the salt in 990 ml. of water. This was sprayed on clumps of oxalis, quakegrass, crabgrass and nimblewill growing in a lawn of primarily fescue grass. The oxalis shriveled up and turned brown within a day. The quakegrass turned a grayish color within two days and within five days was shriveled and dead. The nimblewill and crabgrass turned brown within two days and were dead after seven days. The daytime temperature at the time of spraying was about 85° F. None of the surrounding desirable grass was affected by the treatment nor did any of the treated weeds grow back.

EXAMPLE 2

A similar experiment to Example 1 was run using 1% diammonium ethylenediaminetetraacetate. The results were the same. Subsequently, large patches of nimblewill in turf grass were treated with 1% diammonium EDTA salt solution. Within two weeks, all of the treated nimblewill was dead without any effect on the rest of the lawn.

EXAMPLES 3, 4 AND 5

Water solutions of 3% sodium citrate, 3% potassium citrate and 3% trisodium nitrilotriacetate were prepared by dissolving 30 g. of each salt respectively in 970 ml. of water. Each solution was then sprayed on separate clumps of quakegrass. In each case the treated weeds shriveled and died within a week. No surrounding plants were affected.

EXAMPLE 6

A solution of 2% tetrasodium EDTA was sprayed on burmudagrass growing along a sidewalk and in cracks in the sidewalk. Within five days the bermudagrass had turned brown and started to shrivel but some green was still present. The bermudagrass was retreated and in another week it was completely dead. None of the treated bermudagrass grew back nor were any of the other plants in the sprayed area affected.

EXAMPLE 7

A 10% solution of diammonium glutarate was prepared by neutralizing 50 g. of glutaric acid in water with aqueous ammonium hydroxide and bringing the final solution to 500 ml. with water. This was sprayed on wild ivy and quakegrass. Both were dead within 36 hours.

None of the solutions described in any of Examples 1–7 had any effect when sprayed on perennial ryegrass, azaleas, pachysandra, vinca minor, liriope, English ivy, fern, lily-of-the-valley, and other similar desirable plants. This demonstrates the selective nature of the herbicides of the invention.

EXAMPLE 8

A 5% solution of dimethylammonium glycolate was prepared by dissolving 25 g. Of anhydrous glycolic acid in 400 ml. Of water and then adding 40% dimethylamine in water until a pH of 7 was reached as indicated by pH paper. The solution was then made up to 500 ml. with more water and a few drops of Ivory conc. detergent added. The solution was then sprayed on lawn grass invaded by the weeds oxalis, quakegrass, nimblewill and speedwell. Within 24 hrs, the oxalis was brown and shriveled. The nimblewill and speedwell turned gray and appeared dried out. The quakegrass leaves were curled and also appeared dried out. In a week all of the weeds were brown and dried up and appeared dead. The grass was unaffected.

EXAMPLE 9

A 5% solution of dimethylammonium lactate was prepared as described in Example 7 using lactic acid instead of glycolic acid. This solution was sprayed on quakegrass in turf in one location and on nimblewill turf in another. Within a week, most of the quakegrass leaves had turned white but some of the plants were still green. The area was sprayed again with the same solution. In another week all of the quakegrass was dead. No other vegetation was affected. In the nimblewill plot, most of the sprayed weeds turned brown in a week but not all of the nimblewill was dead. Another spraying was made. In another week, the rest died.

EXAMPLE 10

A patch of quakegrass growing among lily-of-the-valley, liriope, wild strawberries and fern was sprayed with a water solution of sodium gluconate. Within a week, the quakegrass leaves appeared burned on the edges but the plants were not dead. The plants were sprayed again. In several days, the burned appearance of the leaves increased. A third spraying was made which caused all of the quakegrass to turn brown and withered. None of the other vegetation was affected in any way.

EXAMPLE 11

A solution was prepared by dissolving 10 g. of diammonium ethylenediamine tetraacetic acid in 450 ml. of 50% isopropanol. This solution was then sprayed on crabgrass. In two days, the crabgrass turned brown and shriveled. In four days, it appeared to be completely dead. This demonstrates that not all of the acid groups in a complexing acid need to be in the salt form for the complexing compound to be an effective herbicide.

What is claimed is:

1. A method for the control of undesired vegetation which comprises applying to the locus of the undesired vegetation a herbicidally effective amount of a selective herbicidal aqueous composition consisting essentially of a salt of a carboxylic or phosphonic acid capable of forming a stable coordination compound with calcium or magnesium ions.

2. The method of claim 1, wherein the salt of the carboxylic or phosphonic acid is a salt of an acid selected from aminopolycarboxylic acids, aliphatic carboxylic acids, hydroxycarboxylic acids, amino acids, ether polycarboxylic acids, phosphonic acids and polyphosphonic acids.

3. The method of claim 2, wherein the salt is sodium, potassium, lithium, or ammonium.

4. The method of claim 3, wherein the acid is ethylene diamine tetraacetic acid.

5. The method of claim 2, wherein the aminopolycarboxylic acid is ethylenediaminetetraacetic acid, nitrilotriacetic acid, iminodiacetic acid, N-(2-hydroxyethyl) iminodiacetic acid, diethylenetriaminepentaacetic acid, N-(2-hydroxyethyl)ethylenediaminetriacetic acid or glycol ether diaminetetraacetic acid.

6. The method of claim 2, wherein the aliphatic carboxylic acid is oxalic acid, succinic acid, glutaric acid or pyruvic acid.

7. The method of claim 2, wherein the amino acid is glycine, alanine or lysine.

8. The method of claim 2, wherein the phosphonic acid is iminodimethylphosphonic acid, alkyldiphosphonic acid or polyphosphonic acid.

9. The method of claim 2, wherein the hydroxycarboxylic acid is malic acid, citric acid, glycolic acid, lactic acid or tartaric acid.

10. The method of claim 2, wherein the salt of the carboxylic or phosphonic acid is a salt of the formula $N(R)_3$ or $N(R)_4^+$ wherein R is independently selected from hydrogen or a $C_1$–$C_8$ alkyl group, a $C_6$–$C_{14}$ aryl group or a $C_7$–$C_{16}$ alkaryl or alkaryl group.

11. The method of claim 2, wherein the undesired vegetation is oxalis, quakegrass, crabgrass, bermudagrass, nimblewill, or speedwell.

12. The method of claim 2, wherein the composition further contains a surfactant.

13. The method of claim 12, wherein the surfactant is non-ionic or anionic.

14. The method of claim 12, wherein the surfactant is an ethylene oxide condensate, lignosulfonate, ammonium salt of mixtures of aromatic sulphone sulphonic acids condensed with formaldehyde, 1-hydroxyethyl-2-heptadecenyl gloxalidin or an amine oxide.

15. A method for controlling undesired vegetation which comprises:

a. preparing an aqueous solution consisting essentially of a salt of an acid capable of forming a stable coordination compound with calcium or magnesium ion; and b. applying a herbicidally effective amount of said solution to the leaves of the undesired vegetation.

16. The method of claim 15, wherein the acid is an aminopolycarboxylic acid, an aliphatic carboxylic acid, a hydroxycarboxylic acid, an amino acid, an ether polycarboxylic acid, a phosphonic acid or a polyphosphonic acid, and the salt is at least one ion selected from the group consisting of sodium, potassium, lithium, and ammonium.

17. A method for the control of undesired vegetation which comprises applying to the locus of the undesired vegetation a selective, aqueous herbicidal composition consisting essentially of a carboxylic or phosphonic acid salt which is the reaction product of:

(A) lithium hydroxide, sodium hydroxide, sodium carbonate, sodium bicarbonate, potassium hydroxide, ammonium hydroxide, amine or quaternary ammonium hydroxide; and (B) oxalic acid, succinic acid, glutaric acid, pyruvic acid, glycine, alanine, lysine, malic acid, citric acid, glycolic acid, lactic acid, tartaric acid, iminodimethylphosphonic acid, alkyldiphosphonic acid or polyphosphonic acid.

18. The method of claim 17, wherein the aqueous composition further contains a surfactant.

19. The method of claim 17, wherein the weight percent of carboxylic or phosphonic acid salt in the aqueous composition is between from about 1 to about 10 weight percent.

20. The method of claim 17, wherein the undesired vegetation is oxalis, quakegrass, crabgrass, bermudagrass, nimblewill, or speedwell.

* * * * *